United States Patent [19]
Bytyn

[11] Patent Number: 5,635,627
[45] Date of Patent: Jun. 3, 1997

[54] CARBON MONOXIDE SENSOR HAVING MERCURY DOPED ELECTRODES

[75] Inventor: Wilfried Bytyn, Bochum, Germany

[73] Assignee: Endress + Hauser Conducta Gesellschaft fuer Mess—und Regeltechnik mbH + Co., Gerlingen, Germany

[21] Appl. No.: 450,278

[22] Filed: May 25, 1995

[30] Foreign Application Priority Data

May 26, 1994 [EP]  European Pat. Off. ............ 94108150

[51] Int. Cl.$^6$ .................... G01N 27/00; G01N 27/49; G01N 33/00
[52] U.S. Cl. .................. 73/31.05; 73/23.31; 73/31.07; 204/412; 204/415; 204/431; 204/432
[58] Field of Search .................... 73/23.2, 23.31, 73/31.01, 31.05, 31.07; 204/412, 415, 431, 432

[56] References Cited

U.S. PATENT DOCUMENTS

| | | |
|---|---|---|
| 4,051,006 | 9/1977 | Neti et al. .................... 204/412 X |
| 4,478,704 | 10/1984 | Miyoshi et al. .................... 204/412 |
| 4,642,172 | 2/1987 | Fruhwald . |
| 5,284,566 | 2/1994 | Cuomo et al. .................... 204/412 |
| 5,331,310 | 7/1994 | Stetter et al. .................... 340/632 |
| 5,466,356 | 11/1995 | Schneider et al. .................... 204/412 X |

FOREIGN PATENT DOCUMENTS

| | | |
|---|---|---|
| 0084935 | 8/1983 | European Pat. Off. . |
| 3910038 | 2/1991 | Germany . |
| 2122354 | 4/1983 | United Kingdom . |

*Primary Examiner*—Hezron E. Williams
*Assistant Examiner*—Daniel S. Larkin
*Attorney, Agent, or Firm*—Bose McKinney & Evans

[57] ABSTRACT

In this carbon monoxide sensor, particularly for measuring carbon monoxide in flue gases, which must be operated in a controlled-potential bias circuit and which comprises a working electrode, a counter electrode, and a reference electrode, all of platinum black, as well as an electrolyte connected with these three electrodes, the hydrogen cross-sensitivity is drastically reduced by providing two layers enriched by mercury and/or mercury ions, one on a surface of the working electrode and one of a surface of the reference electrode. These two electrodes are treated with mercury or a mercury compound before or after incorporation into the sensor.

6 Claims, 1 Drawing Sheet

CARBON MONOXIDE SENSOR HAVING MERCURY DOPED ELECTRODES

FIELD OF THE INVENTION

The present invention relates to carbon monoxide sensors which are operated in a controlled-potential bias circuit, cf., for example, U.S. Pat. No. 4,642,172, and have three electrodes.

BACKGROUND OF THE INVENTION

Such electrochemical three-electrode carbon monoxide sensors, which are already available commercially, are sensitive not only to the gas to be measured, i.e., carbon monoxide (CO), but also to molecular hydrogen ($H_2$), which is contained particularly in flue gases, for example. This is referred to as "hydrogen cross-sensitivity" of the carbon monoxide sensor.

This hydrogen cross-sensitivity is due to the fact that at the electrodes, which are made of platinum black, not only the oxidation of carbon monoxide, but also that of hydrogen occurs very rapidly. In the case of commercially available carbon monoxide sensors, the cross-sensitivity is 30% to 100%, referred to the carbon monoxide sensitivity.

Electrochemically, the hydrogen cross-sensitivity is due to the fact that the oxidation of carbon monoxide on platinum occurs sufficiently rapidly only at a working electrode potential of approximately 800 mV to 900 mV, referred to a standard hydrogen electrode, since a certain oxygenation of the platinum surface is necessary for the carbon monoxide oxidation. By contrast, hydrogen oxidation occurs ideally already at 0 mV and actually in response to small overvoltages in the range of 0 mV to 200 mV, referred to the aforementioned standard hydrogen electrode.

Thus, by suitable choice of the electrochemical potential, hydrogen can, in the ideal case, be measured at pure platinum electrodes cross-sensitivity free in addition to carbon monoxide, while the hydrogen signal is always superimposed on the carbon monoxide signal. With commercially available electrochemical three-electrode carbon monoxide sensors, therefore, carbon monoxide is not measurable hydrogen cross-sensitivity free at a constant working potential (approximately 1 V with respect to the standard hydrogen electrode).

Besides being used for flue gas analysis, carbon monoxide sensors are employed to monitor air quality in basement garages and tunnels and to detect smoldering fires.

In Germany, performance tests of flue gas analyzers must be carried out in accordance with a guideline of the Central Association of the (German) Chimney Sweepers' Guild. According to that guideline, the measurement uncertainty in the measuring range greater than 400 ppm carbon monoxide must not exceed ±5% of the measured value. This means that the hydrogen cross-sensitivity of such carbon monoxide sensors used for flue gas measurements must be less than 5%, referred to the carbon monoxide main sensitivity of such sensors. However, this value is not attainable with conventional three-electrode carbon monoxide sensors.

Therefore, a compound gas sensor with a carbon monoxide measuring portion and a hydrogen measuring portion is on the market. The output of the hydrogen measuring portion serves to electronically compensate for the hydrogen cross-sensitivity of the carbon monoxide measuring portion. This compound gas sensor has, in addition to the three electrodes, a second working electrode for measuring hydrogen, which, as viewed from the gas inlet, is disposed behind the (first) working electrode for measuring carbon monoxide.

If this commercially available compound gas sensor is to be operated without microprocessor controlled compensation electronics which are additionally offered by the manufacturer, it must be calibrated with carbon monoxide or hydrogen calibration gas, if necessary at different temperatures. This, of course, is troublesome and time consuming.

SUMMARY OF THE INVENTION

By contrast, the invention solves the problem of reducing the hydrogen cross-sensitivity of a three-electrode gas sensor by providing a special design of the same.

To accomplish this, the invention, on the one hand, provides a carbon monoxide sensor, particularly for measuring carbon monoxide in flue gases, which must be operated in a controlled-potential bias circuit, said carbon monoxide sensor comprising:

- a working electrode of platinum black;
- a counter electrode of platinum black;
- a reference electrode of platinum black;
- an electrolyte connected with the working electrode, the counter electrode, and the reference electrode; and
- two layers enriched by mercury and/or mercury ions, one on a surface of the working electrode and one on a surface of the reference electrode.

In a preferred embodiment, each of the layers enriched by mercury and/or mercury ions is few atomic layers thick.

On the other hand, the invention provides a method of manufacturing a carbon monoxide sensor, particularly for measuring carbon monoxide in flue gases, which must be operated in a controlled-potential bias circuit, said carbon monoxide sensor comprising

- a working electrode of platinum black;
- a counter electrode of platinum black;
- a reference electrode of platinum black; and
- an electrolyte connected with the working electrode, the counter electrode, and the reference electrode; said method comprising the step of treating the working electrode and the reference electrode with mercury or a mercury compound before and/or after incorporation into the carbon monoxide sensor.

In a preferred embodiment of this method, the surfaces treated with mercury or a mercury compound are reduced for amalgamation.

GB-A2 122 354 describes a three-electrode hydrogen sensor in which the reference electrode comprises a platinum wire embedded in a paste of mercury and mercurous sulfate, and in which the working electrode comprises a pure gold wire, while the counter electrode comprises a lead disc. GB-A-2 122 354 thus describes a gas sensor for sensing hydrogen, not a carbon monoxide sensor.

The inventor found to his surprise that the hydrogen sensitivity of carbon monoxide sensors can be drastically reduced by designing the working electrode and the reference electrode as platinum black electrodes and by treating these two electrodes with mercury or a mercury containing compound, with a sufficient carbon monoxide main sensitivity being preserved, of course.

The invention will become more apparent from the following description of an embodiment taken in conjunction with the accompanying drawing, in which:

DETAILED DESCRIPTION

Figure 1:
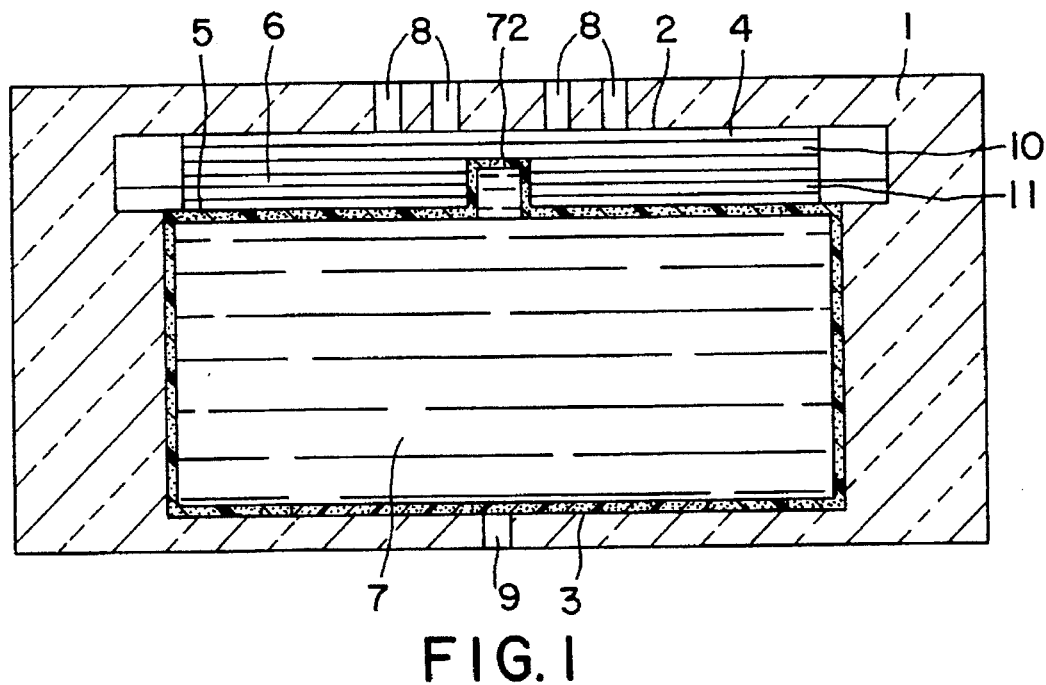
FIG. 1 is a schematic cross sectional view of a carbon monoxide sensor.
Figure 2:
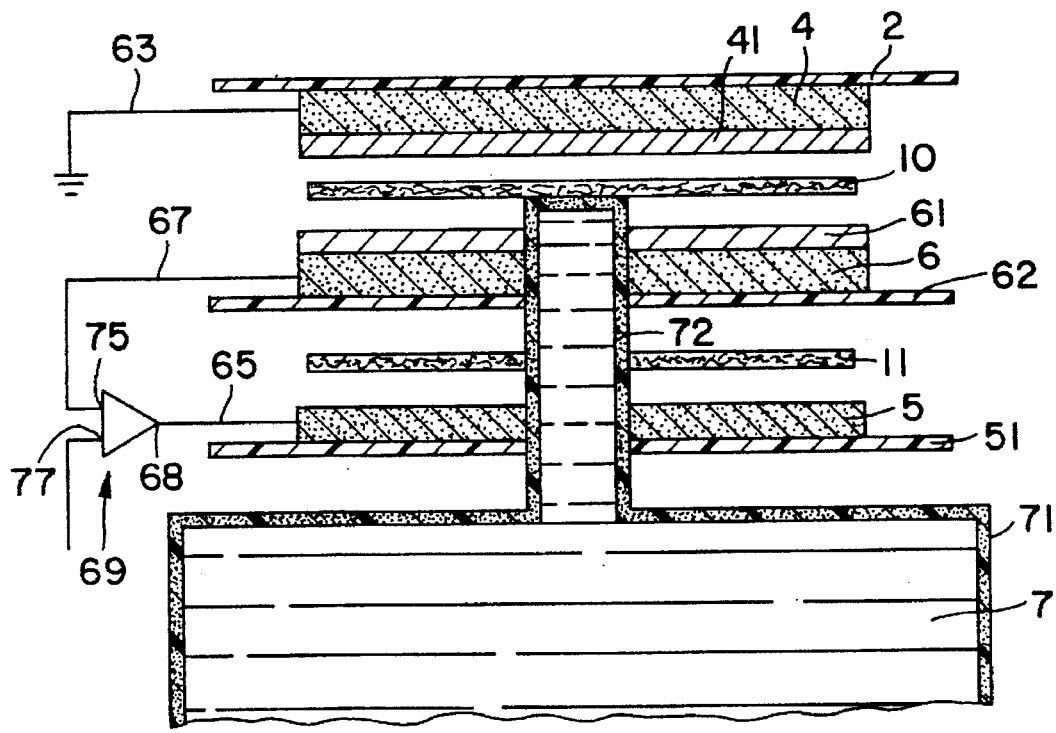
FIG. 2 is an exploded enlarged cross sectional view (not to scale) of the electrode portion of the carbon monoxide sensor of FIG. 1.

The carbon monoxide sensor shown in FIGS. 1 and 2 comprises a housing 1 of a suitable material, which may include glass. The housing 1 has, at opposite sides, openings 8 and 9 which are closed, respectively, with first and second diaphragms 2 and 3 that are permeable to gas, but impermeable to electrolytes. A suitable material for the diaphragms 2, 3 is polytetrafluoroethylene. The second diaphragm 3 is at least permeable to oxygen, so that oxygen required for the electrochemical reaction can enter the interior of the carbon monoxide sensor.

A porous working electrode 4 of platinum black is deposited on the inside of the first diaphragm 2. In the aforementioned controlled-potential bias circuit, this working electrode 4 must be connected to ground. The first diaphragm 2 thus also serves as a support for the working electrode 4. The diaphragm 2 must at least be permeable to the carbon monoxide to be measured, so it is also permeable to hydrogen.

To minimize the hydrogen cross-sensitivity, the surface of the working electrode 4 remote from the diaphragm 2 is provided with a layer 41 enriched with mercury and/or with mercury ions, which preferably has a thickness of few atomic layers, i.e., a thickness approximately on the order of $10^{-10}$ m.

A reference electrode 6 of platinum black is placed adjacent to the working electrode 4, and is positioned so that the mercury layer 41 of the working electrode 4 is disposed between the working electrode 4 and the reference electrode 6. Filter paper 10 is interposed between the mercury layer 41 and the reference electrode 6. The reference electrode 6 is disposed on a support 62, which may also be of polytetrafluoroethylene, for example. In a similar manner as in the case of the working electrode 4, a layer 61 enriched with mercury and/or with mercury ions is provided on the surface of the reference electrode 6 remote from the support 62 to minimize the hydrogen cross-sensitivity. This layer 61, too, preferably has a thickness of few atomic layers, i.e., a thickness approximately on the order of $10^{-10}$ m.

A counter electrode 5 of platinum black is provided adjacent to the reference electrode 6. The counter electrode 5 is positioned so that the support 62 for the reference electrode 6 is placed between the counter electrode 5 and the reference electrode 6. A further filter paper 11 is interposed between the support 62 and the counter electrode 5. A support 51 is provided for the counter electrode 5. The support 51 is disposed on a side of the counter electrode 5 remote from the filter paper 11. The support 51 is preferably comprised of polytetrafluoroethylene, similar to supports 2 and 62.

The layers 41, 61 enriched with mercury and/or with mercury ions face toward and touch the filter paper 10, i.e., the reference electrode 6 and the working electrode 4 are mirror symmetrical with respect to the filter paper 10. Similarly, the support 62 of the reference electrode 6 and the platinum black of the counter electrode 5 touch the interposed filter paper 11.

The leads 63, 65, 67 of the three electrodes 4, 5, 6 are illustrated schematically in FIG. 2. These leads can be platinum wires, for example., which are embedded or inserted at one end in the platinum black of the respective electrodes and are brought out through the wall of the housing 1, so that the carbon monoxide sensor can be operated in the afore-mentioned controlled-potential bias circuit.

In this circuit, the counter electrode 5 must be connected to the output 68 of an operational amplifier 69, while the reference electrode 6 must be coupled to the noninverting input 75 of this operational amplifier, whose inverting input 77 must be supplied with a constant voltage, V the so called sensor voltage.

The greater part of the interior of the housing 1 contains an electrolyte 7, e.g., sulfuric acid, particularly 10N (i.e., 40-percent) sulfuric acid. For this there may be provided a porous body 71 of, e.g., a suitable plastic which is impregnated with the electrolyte 7.

In FIGS. 1 and 2, the counter electrode 5, the reference electrode 6, and the filter paper 11 has a central hole into which extends a projecting portion 72 of the body 71. Additionally, the surface of the projecting portion 72 engages the surface of the filter paper 10. Thus, the electrolyte 7 reaches the filter papers 10, 11 and is, therefore, also connected with the three electrodes, so that the electrochemical processes underlying the carbon monoxide measurement can take place.

To form the layers 41, 61 enriched with mercury and/or with mercury ions, the respective platinum black of the working electrode 4 and the reference electrode 6 is treated with mercury or a mercury compound, such as mercury salt, before or after incorporation into the carbon monoxide sensor. This may be followed by a further treatment, such as a reduction for amalgamation.

Through the mercury treatment, the respective surfaces of the working electrode and the reference electrode are doped with mercury or, in other words, selectively poisoned for hydrogen. In this manner, tunnelling of the hydrogen through the working electrode 4 and the reference electrode 6 is to be achieved without catalytic conversion; thus, in the ideal case, no hydrogen conversion is to occur not only at the reference electrode 6, but also at the working electrode 4.

As measurements on carbon monoxide sensors constructed according to FIGS. 1 and 2 have shown, the hydrogen cross-sensitivity, which ranges between 20% and 100% in the temperature range of $-15°$ C. to $+40°$ C. without the mercury treatment, can be reduced to values of practically 0% at temperatures of $-15°$ C. to $+20°$ C. and to values of 0% to 5% at temperatures of $+20°$ C. to $+40°$ C., with a sufficient carbon monoxide main sensitivity of the carbon monoxide sensor being preserved.

Instead of providing the counter electrode 5 and the reference electrode 6 as well as the filter papers 10, 11 with respective central holes for passing the projecting portion 72 of the body 71 therethrough as shown in FIGS. 1 and 2, it is possible to leave the counter electrode 5 and the reference electrode 6 as well as the filter papers 10, 11 unholed.

In that case, the body 71, instead of being provided with the projecting portion 72, must have a depression into which the layers of electrodes and filter paper must be placed in the order shown in FIGS. 1 and 2. The electrolyte is now supplied to the electrodes from the edge of the depression via the filter papers.

I claim:

1. A carbon monoxide sensor, for measuring carbon monoxide in flue gases, the carbon monoxide sensor comprising:

a working electrode of platinum black;

a counter electrode of platinum black;

a reference electrode of platinum black; each of the working electrode, and reference electrode including a carbon monoxide contacting surface;

an electrolyte connected with the working electrode, the counter electrode and the reference electrode; and two layers enriched by mercury and/or mercury ions, one on the carbon monoxide contacting surface of the working electrode and one on the carbon monoxide contacting surface of the reference electrode.

2. A carbon monoxide sensor as claimed in claim 1 wherein each of the layers enriched by mercury and/or mercury ions is few atomic layers thick.

3. A method of manufacturing a carbon monoxide sensor, for measuring carbon monoxide in flue gases, the carbon monoxide sensor comprising a working electrode of platinum black;

a counter electrode of platinum black; a reference electrode of platinum black; each of the working electrode, counter electrode and reference electrode including a carbon monoxide contacting surface, and an electrolyte connected with the working electrode, the counter electrode, and the reference electrode; said method comprising the step of treating the carbon monoxide contacting surfaces of the working electrode and the reference electrode with mercury or a mercury compound.

4. A method as claimed in claim 3 wherein the surfaces treated with mercury or a mercury compound are reduced for amalgamation.

5. The method as claimed in claim 3 wherein at least one of the working electrode and reference electrode are treated with mercury or a mercury compound before incorporation into the carbon monoxide sensor.

6. The method as claimed in claim 3 wherein at least one of the working electrode and reference electrode are treated with mercury or a mercury compound after incorporation into the carbon monoxide sensor.

* * * * *